(12) United States Patent
Nielsen et al.

(10) Patent No.: US 11,337,014 B2
(45) Date of Patent: May 17, 2022

(54) EARPIECE FOR A HEARING DEVICE AND METHOD OF PRODUCING AN EARPIECE

(71) Applicant: GN HEARING A/S, Ballerup (DK)

(72) Inventors: Henrik Nielsen, Roskilde (DK); Jan Johansen, Koge (DK)

(73) Assignee: GN HEARING A/S, Ballerup (DK)

( * ) Notice: Subject to any disclaimer, the term of this patent is extended or adjusted under 35 U.S.C. 154(b) by 0 days.

(21) Appl. No.: 16/596,721

(22) Filed: Oct. 8, 2019

(65) Prior Publication Data
US 2020/0145768 A1 May 7, 2020

(30) Foreign Application Priority Data

Nov. 5, 2018 (EP) .................................. 18204470

(51) Int. Cl.
*H04R 25/00* (2006.01)
*A61B 5/024* (2006.01)
*A61B 5/00* (2006.01)

(52) U.S. Cl.
CPC ....... *H04R 25/652* (2013.01); *A61B 5/02427* (2013.01); *A61B 5/6817* (2013.01); *H04R 25/609* (2019.05); *H04R 25/658* (2013.01); *H04R 2225/021* (2013.01); *H04R 2225/025* (2013.01)

(58) Field of Classification Search
USPC ................. 381/312, 315, 324, 328
See application file for complete search history.

(56) References Cited

U.S. PATENT DOCUMENTS

| | | | | |
|---|---|---|---|---|
| 7,233,676 B2 * | 6/2007 | Bayer | .................... | H04R 25/65 381/328 |
| 9,036,854 B2 * | 5/2015 | Lewis | .................... | H04R 5/023 381/381 |
| 10,175,753 B2 * | 1/2019 | Boesen | ................ | H04R 1/1016 |
| 2003/0002705 A1 * | 1/2003 | Boesen | ............... | H04M 1/6066 381/380 |
| 2007/0071262 A1 | 3/2007 | Rass | | |

(Continued)

FOREIGN PATENT DOCUMENTS

EP 3056018 B1 6/2019
WO WO 2017/054875 A1 4/2017

OTHER PUBLICATIONS

Extended European Search Report dated Dec. 21, 2018 for corresponding European Application No. 18204470.1.

*Primary Examiner* — Suhan Ni
(74) *Attorney, Agent, or Firm* — Vista IP Law Group, LLP

(57) ABSTRACT

An earpiece for a hearing device includes: an ear canal part to be introduced into an ear canal of a user, the ear canal part comprising a first contact surface configured to contact a superior part of the ear canal of the user; a primary sensor, where the primary sensor is configured to measure signals from a skin surface of the user; and a support structure comprising a first part and a second part, wherein the first part of the support structure is attached to the ear canal part, wherein the second part of the support structure is attached to the primary sensor, and wherein the second part of the support structure is configured to position the primary sensor in an inferior concha cava of the user; wherein the support structure is configured to apply a force to press the primary sensor towards the skin surface of the user.

21 Claims, 6 Drawing Sheets

(56) References Cited

U.S. PATENT DOCUMENTS

2015/0281856 A1* 10/2015 Park .................... H04R 25/505
                                                        381/320
2022/0007118 A1*  1/2022 Rucker ................. H02J 7/007

* cited by examiner

EARPIECE FOR A HEARING DEVICE AND METHOD OF PRODUCING AN EARPIECE

RELATED APPLICATION DATA

This application claims priority to, and the benefit of, European Patent Application No. 18204470.1 filed on Nov. 5, 2018. The entire disclosure of the above application is expressly incorporated by reference herein.

FIELD

The present disclosure relates to an earpiece for a hearing device and a method of producing an earpiece for a hearing device.

BACKGROUND

There is a general need for devices that are capable of monitoring health data from users at any time, and where it is helpful for healthcare professionals and users to have access to data that may be continuously obtained from the user. A hearing device is a device which is well known to a user, and can either be worn continuously as a hearing aid or intermittently as a headset. Thus, the introduction of monitoring devices into a hearing device may make it easy for the user to provide health data monitoring, while maintaining comfort for the user.

The introduction of health monitoring into an earphone has previously been disclosed in WO 2018/175196, where an earpiece uses a stabilizer to hold the earpiece in position in the ear. This stabilizer, which contacts the outer ear of the user has been shown as causing discomfort when wearing over a long period.

SUMMARY

Accordingly, there is a need for an earpiece for a hearing device, where the earpiece does not put strain on the ear of the user.

An earpiece for a hearing device is disclosed, the earpiece comprising: an ear canal part to be introduced into the ear canal of a user, the ear canal part comprising a first contact surface configured to contact the superior part of the ear canal of the user; a primary sensor, where the primary sensor is configured to measure signals from a skin surface of the user; and a support structure comprising a first part and a second part, wherein the first part is attached to the ear canal part and the second part is attached to the primary sensor, and wherein the second part of the support structure is configured to position the primary sensor in the inferior concha cava during use of the hearing device earpiece, and wherein the support structure is configured to transmit a force from the superior part of the ear canal to the skin contacting surface of the primary sensor.

An advantage of an earpiece in accordance with the disclosure is that the transfer of the force from the superior part of the ear canal via the first contact surface, to the primary sensor that is positioned in the inferior concha cava via the support structure, ensures that the force is applied in a direction towards the inferior concha cava, in turn securing the primary sensor in the concha cava.

Another advantage is that the earpiece is capable of maintaining its position during use, as the opposing force between the first contact surface and the concha cava can fix the earpiece in its position.

Another advantage is that the earpiece is capable of monitoring the physical data from the user, which may e.g. be utilized for physical training purposes or for health monitoring that can be utilized by health care professionals, or any other purpose where it may be advantageous to monitor specific physical conditions of the user.

An advantage of the earpiece in accordance with the disclosure is that by applying a force between the inferior concha cava and the superior part of the ear canal it is possible to reduce the application of force to the outer ear of the user, in turn reducing discomfort when wearing the earpiece while allowing precise and accurate measurements with the primary sensor.

Also disclosed is a method of producing an earpiece for a hearing device of a user, where the method comprises: obtaining primary data representative of a position of at least part of the superior part of the ear canal of the user; obtaining secondary data representative of a position of the inferior concha cava of the user, manufacturing an ear canal part and a support structure for a primary sensor based on the primary data and the secondary data, wherein the ear canal part and the support structure is configured to transmit a force from the superior part of the ear canal of the user to the inferior concha cava.

The present disclosure allows for improved earpiece where the support structure and the earpiece are improved for long time comfort for the user. The continuous application of force to the outer ear of the user may, similar to what is shown in e.g. WO 2018/175196 may e.g. result in fatigue or discomfort in the area where the force is applied, as the stabilizer applies a force to a soft part of the ear, i.e. the Superior crus of antihelix, the cymba, or the helix, in order to provide a force to a sensor to the ear of the user.

BRIEF DESCRIPTION OF THE DRAWINGS

The above and other features and advantages will become readily apparent to those skilled in the art by the following detailed description of exemplary embodiments thereof with reference to the attached drawings, in which.

DETAILED DESCRIPTION

Figure 1A:
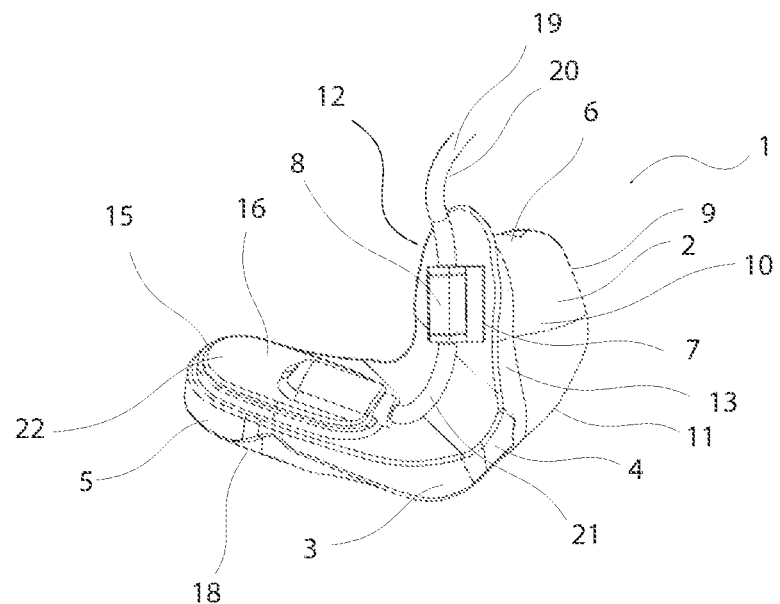
FIGS. 1a and 1b shows an exemplary earpiece.

Various exemplary embodiments and details are described hereinafter, with reference to the figures when relevant. It should be noted that the figures may or may not be drawn to scale and that elements of similar structures or functions are represented by like reference numerals throughout the figures. It should also be noted that the figures are only intended to facilitate the description of the embodiments. They are not intended as an exhaustive description of the invention or as a limitation on the scope of the invention. In addition, an illustrated embodiment needs not have all the aspects or advantages shown. An aspect or an advantage described in conjunction with a particular embodiment is not necessarily limited to that embodiment and can be practiced in any other embodiments even if not so illustrated, or if not so explicitly described.

A hearing device is disclosed. The hearing device may be a hearable or a hearing aid, wherein the processor is configured to compensate for a hearing loss of a user.

The hearing device may be of the behind-the-ear (BTE) type, in-the-ear (ITE) type, in-the-canal (ITC) type, receiver-in-canal (RIC) type or receiver-in-the-ear (RITE) type. The hearing aid may be a binaural hearing aid. The hearing device may comprise a first earpiece and a second earpiece, wherein the first earpiece and/or the second earpiece is an earpiece as disclosed herein. The hearing device could be a microphone in the ear device, where the microphone may face in/out the ear canal. The hearing device may include two microphones in an ITE housing, one facing inwards and the other facing outwards.

The hearing device may be configured for wireless communication with one or more devices, such as with another hearing device, e.g. as part of a binaural hearing system, and/or with one or more accessory devices, such as a smartphone and/or a smart watch. The hearing device optionally comprises an antenna for converting one or more wireless input signals, e.g. a first wireless input signal and/or a second wireless input signal, to antenna output signal(s). The wireless input signal(s) may origin from external source(s), such as spouse microphone device(s), wireless TV audio transmitter, and/or a distributed microphone array associated with a wireless transmitter. The wireless input signal(s) may origin from another hearing device, e.g. as part of a binaural hearing system, and/or from one or more accessory devices.

The hearing device optionally comprises a radio transceiver coupled to the antenna for converting the antenna output signal to a transceiver input signal. Wireless signals from different external sources may be multiplexed in the radio transceiver to a transceiver input signal or provided as separate transceiver input signals on separate transceiver output terminals of the radio transceiver. The hearing device may comprise a plurality of antennas and/or an antenna may be configured to be operate in one or a plurality of antenna modes. The hearing device may optionally be utilized for different wireless communication systems/protocols such as Magnetic induction (MI), telecoil, BlueTooth™, WiFi, NFC and cellular network etc. The transceiver input signal optionally comprises a first transceiver input signal representative of the first wireless signal from a first external source.

The hearing device comprises a set of microphones. The set of microphones may comprise one or more microphones. The set of microphones comprises a first microphone for provision of a first microphone input signal and/or a second microphone for provision of a second microphone input signal. The set of microphones may comprise N microphones for provision of N microphone signals, wherein N is an integer in the range from 1 to 10. In one or more exemplary hearing devices, the number N of microphones is two, three, four, five or more. The set of microphones may comprise a third microphone for provision of a third microphone input signal.

The hearing device optionally comprises a pre-processing unit. The pre-processing unit may be connected to the radio transceiver for pre-processing the transceiver input signal. The pre-processing unit may be connected the first microphone for pre-processing the first microphone input signal. The pre-processing unit may be connected the second microphone if present for pre-processing the second microphone input signal. The pre-processing unit may comprise one or more A/D-converters for converting analog microphone input signal(s) to digital pre-processed microphone input signal(s).

The hearing device comprises a processor for processing input signals, such as pre-processed transceiver input signal and/or pre-processed microphone input signal(s). The processor provides an electrical output signal based on the input signals to the processor. Input terminal(s) of the processor are optionally connected to respective output terminals of the pre-processing unit. For example, a transceiver input terminal of the processor may be connected to a transceiver output terminal of the pre-processing unit. One or more microphone input terminals of the processor may be connected to respective one or more microphone output terminals of the pre-processing unit.

The hearing device comprises a processor for processing input signals, such as pre-processed transceiver input signal(s) and/or pre-processed microphone input signal(s). The processor is optionally configured to compensate for hearing loss of a user of the hearing device. The processor provides an electrical output signal based on the input signals to the processor. Input terminal(s) of the processor are optionally connected to respective output terminals of the pre-processing unit. For example, a transceiver input terminal of the processor may be connected to a transceiver output terminal of the pre-processing unit. One or more microphone input terminals of the processor may be connected to respective one or more microphone output terminals of the pre-processing unit.

In accordance with the disclosure, there may be provided an earpiece for a hearing device, where the earpiece may comprise: an ear canal part to be introduced into the ear canal of a user, the ear canal part comprising a first contact surface configured to contact the superior part of the ear canal of the user; a primary sensor, where the primary sensor is configured to measure signals from a skin surface of the user; and a support structure comprising a first part and a second part, wherein the first part is attached to the ear canal part and the second part is attached to the primary sensor, and wherein the second part of the support structure is configured to position the primary sensor in the inferior concha cava during use of the hearing device earpiece, and wherein the support structure is configured to transmit a force from the superior part of the ear canal to the skin contacting surface of the primary sensor.

The skin surface of inferior concha cava and the skin surface of the superior part of the ear canal face each other, which means that the force may engage both surfaces in a direction of a substantially straight line. This means that when the force is applied between the two skin surfaces, the skin surfaces provide an opposing force, where the force may be seen as a static force. This increases the likelihood that the primary sensor is maintained in its position, when the earpiece is positioned in the ear of the user. It has been found out that the magnitude of the force is preferably low, as any force that is applied to the ear of a user has a tendency of becoming uncomfortable to the user. The force should be configured to be high enough to ensure that the earpiece can stay in its position during use, while low enough to minimize the risk that the earpiece becomes uncomfortable to the user. This force may differ from one person to the other and may also vary on the size of the ear, ear canal, concha cava or other anatomical features of the outer ear. The person skilled in the art of designing and producing earpieces for hearing devices will not have any problem in finding a suitable magnitude of force that is suitable to fulfil the purpose of the earpiece.

The ear canal part of the earpiece may be configured so that the ear canal part is introduced into the ear canal of the user, i.e. that the first contact surface of the ear canal part is positioned beyond the opening of the ear canal, in a medial direction towards the Tympanic membrane. The support structure is attached to the ear canal part in such a manner that the support structure is capable of transferring a compression force from the first contact surface to the first part of the support structure. This means that if a compression force is applied to the support structure, the force is transferred to the first contact surface.

The primary sensor may be configured to measure signals from a skin surface of the user. The primary sensor may be provided with a skin contacting surface, where the skin contacting surface may be positioned in the inferior concha cava during use. The skin contacting surface may be any kind of surface that may come into contact with the surface and may be configured to ensure that a part of the sensor is in contact with the skin surface in any suitable way. The skin contacting surface may be provided with elements that ensure that the sensor measurement is protected from environmental noise, where the environmental noise may be light, sound. The protection may e.g. be in the form of providing a soft skirt, that ensures that light cannot pass a peripheral edge of the measurement part of the sensor, into the area where the sensor measures the physiological data. It may be advantageous to prevent e.g. daylight to pass between the skin of the user and the primary sensor.

In one or more exemplary earpieces, the ear canal part may be a housing having an outer surface, where at least part of the outer surface of the housing may have a shape to match an ear canal surface part of the ear canal. The ear canal part may constructed in such a manner, so at least part of the outer surface of the ear canal part has a shape that corresponds to the inner surface of the ear canal, i.e. the skin surface of the ear canal. By having the ear canal part as a housing, the outer surface of the housing may have a surface area that may be adapted to spread the force to the superior part of the ear canal to a large area, in order to improve comfort and/or stability of the earpiece during use. The size of the area may be between 2 mm$^2$ and 80 mm$^2$, more specifically between 3 mm$^2$ and 60 mm$^2$, more specifically between 4 mm$^2$ and 40 mm$^2$, more specifically between 5 mm$^2$ and 30 mm$^2$.

In one or more exemplary earpieces, the ear canal part may have a second contact surface, where the second contact surface is configured to contact the anterior and/or the posterior part of the ear canal of the user. By applying a further contact surface to the ear canal part, the second contact surface may stabilize the earpiece during use, and may spread the force applied by the earpiece inside the ear canal to more than one parts of the ear canal to improve comfort. The ear canal part may optionally comprise a third contact surface where the third contact surface may be configure to contact the inferior part of the ear canal.

In one or more exemplary earpieces, the ear canal part may comprise a first end having a receiver opening and/or a second end which may be attached to the first end of the support structure. The receiver opening may be an opening where sound may be transmitted from inside the ear canal part to the outside through the first end. By providing the ear canal part with a first end having a receiver opening, means that the ear canal part may be provided with a receiver and or a sound tube, or any possible type of sound transmission option suitable for a hearing device. Thus, the sound transmission from a hearing device may be passed through the ear canal part, either passively where the ear canal part may be provided with a sound tube, and the receiver may be provided in e.g. a BTE hearing aid. Also, the ear canal part may be provided with a receiver, where the receiver is provided inside the ear canal part, and where the sound is transmitted through the receiver opening.

The second end of the ear canal part may be adapted to be connected to the first end of the support structure. By providing an ear canal part that may be connected to the first end of the support structure, the force applied via the support structure from the inferior surface of the concha cava may be transferred via the first end of the support structure to the second end of the ear canal part.

In one or more exemplary earpieces, the receiver may be removably attached to the ear canal part and/or the sensor may be removably attached to the support structure. By providing an ear canal part which may have a receiver that is removably attached, the user may exchange the ear canal part and/or the receiver between uses, for a specific application. For example, if the user has a specific ear canal part for specific activity, such as physical training, the user can change/remove the receiver from the ear canal part and insert the receiver into another ear canal part. Also, the removeable receiver may be usable if the user needs to clean out the ear canal part, if the ear canal part is dirty or drenched in sweat, and subsequently replace the receiver into the ear canal part. This may protect the receiver from damage, if the ear canal part is e.g. cleaned with water or a liquid cleaning agent. The primary sensor may also be removeable from the support structure, where the sensor may be attached and/or removed if necessary. By having a removeable sensor, the sensor may e.g. be replaced if it is not functioning optimally, and a replacement sensor may be attached to the support structure.

In one or more exemplary earpieces, the earpiece further may comprise an electrical wire connecting a receiver and/or the primary sensor to a BTE housing of the hearing device. The electrical wire may provide an electrical connection to the receiver and/or the primary sensor, and the electrical wire may extend from the earpiece to the BTE housing. The wire may be a stiff wire, that may be utilized to maintain the BTE housing in its position behind the ear of the user.

In one or more exemplary earpieces, the support structure may comprise a third part which may be connected to the first and/or the second part, wherein the third part may be configured to contact and transmit a force from a surface area of the outer ear of the user to the skin contacting surface of the primary sensor. The third part may be utilized to provide a further stability to the earpiece, where the third part may be configured to transmit a force from e.g. the helix, the antihelix, fossa or other anatomical parts of the ear. The third part may be utilized to provide an increased stability e.g. during physical activity, in order to improve the retention of the earpiece during use, such as running, so that the user may feel secure during the physical activity and/or to improve the positioning of the sensor during physical activity.

In one or more exemplary earpieces, the primary sensor may be a Photoplethysmogram (PPG) sensor. The PPG sensor may optically obtain a plethysmogram, which is a volumetric measurement of an organ. A PPG sensor may be obtained by using a pulse oximeter which illuminates the skin and measures changes in light absorption. A conventional pulse oximeter monitors the perfusion of blood to the dermis and subcutaneous tissue of the skin. The primary sensor may be utilized to measure the flow of blood below the skin, and the data received from the primary sensor may be utilized to extract data and process the data to obtain a physical data, which may represent a specific physiological condition of the user, such as a heart rate, or where it may be processed further to extract specific data that may show certain physical conditions. It may be advantageous to prevent e.g. daylight to pass between the skin of the user and the primary sensor. Thus, one of the advantages is that the primary sensor may be held in its correct position using the force transmitted via the support structure, so that the PPG sensor (primary sensor) is held in its correct position and does not move relative to the skin surface of the user. Any movement of the primary sensor relative to the skin surface may produce noise artefacts, that may cause the sensor signal, e.g. the PPG signal, to be unusable, or at least parts of the sensor signal to be too noisy to be used.

In one or more exemplary earpieces, the first part and/or the second part of the support structure has a shape that corresponds with at least part of the concha cava of the ear of the user. Thus, it may be possible to allow the support structure to follow the contour of the concha cava, so that the support structure, which extends in a direction from the ear canal towards the concha cava maintains a low profile and does not extend significantly out of the ear of the user. Furthermore, the shape of the support structure may furthermore contact the outer ear of the user, in an area extending from the ear canal opening, towards the inferior concha cava, in order to provide an increased stability, where at least part of the support structure may be in contact with the outer ear of the user.

In one or more exemplary earpieces, the ear canal part may be a custom housing for a specific user corresponding to a 3D shape of the outer ear and/or the ear canal of the user. The provision of a custom housing may ensure that the earpiece fits the user in an optimal manner, where the outer shape of the custom housing may have surfaces that match the surface areas of the outer ear of the user. The custom housing may be formed or moulded using a 3D model of the ear and the ear canal of the user. The support structure may be part of the housing and may be formed together with the housing. This means that the support structure may be formed and structured optimally to hold the ear canal part in its position, as well as maintaining the support structure positioned in such a way, that the force applied between the superior part of the ear canal and the inferior concha cava is optimal for the specific user. I.e. that the force between these two anatomical parts is applied in an optimum manner, thereby reducing risk that the user will have fatigue in the ear when using the earpiece.

In one or more exemplary earpieces, the first contact surface may be a non-elastic first contact surface. The non-elastic first contact surface means that the force that is applied through the ear canal part may be transferred fully towards the superior part of the ear canal, so that the force that is applied from the support structure towards the ear canal part is transferred directly through the ear canal part, without having any loss of force via elasticity of the ear canal part. This effectively means that the first contact surface does not have an elastic part, which is adapted to bend or flex when force is applied to it but may be seen as a rigid contact surface. Thus, the first contact surface of the ear canal part may be rigid. The rigidity of a first contact surface may be viewed in terms of the use of the earpiece, in that it is very common to provide earpieces with a flexible member, that is adapted to enter the ear canal. Within the understanding of the present disclosure, the term rigidity means that prior and during use of the earpiece, the ear canal part maintains its shape, and the insertion of the ear canal part does not change the shape of the ear canal part inside the ear.

In one or more exemplary earpieces, the second part of the support structure may be non-elastic. Thus, the second part of the support structure may be rigid. By providing a non-elastic support structure, the support structure may be formed in such a manner, that the support structure maintains its predetermined shape prior and during use of the earpiece, so that when the earpiece is inserted into the ear of a user, support structure maintains its shape. The non-elastic shape of the second part may ensure that the positioning of the sensor may be maintained during use, and that the force may be applied in a constant manner when the earpiece has been positioned in the ear of the user, and that the force remains constant from the superior part of the ear canal and the inferior concha cava. Thus, when the ear canal part has been introduced into the ear of the user, the support structure maintains its position, and the second part of the support structure does not move relative to the ear canal part.

In one or more exemplary earpieces, the ear canal part may comprise a first cavity for the receiver and/or the support structure may comprise a second cavity for the primary sensor. By providing a first cavity for the receiver and a second cavity for the primary sensor, the receiver and the primary sensor may be removably connected to the earpiece, and e.g. interchanged when necessary. Thus, if a primary sensor or a receiver is damaged or malfunctions it is relatively easy to remove the receiver and/or the primary sensor from their cavities and position a replacement sensor in the same cavity. The cavities may be open cavities, where the cavities provide through going opening from one side of the cavity to the other side of the cavity.

In one or more exemplary earpieces, the ear canal part may comprise a receiver. By providing a receiver in the ear canal part, it may be possible to connect a hearing device to the earpiece via an electrical wire, where the electrical wire may continue towards the primary sensor, so that both the receiver and the primary sensors are electrically connected to the hearing device. Also, the primary sensor and/or the receiver may be provided with separate electrical wires to transmit both power, electrical signals and/or data transmission to the primary sensor and/or the receiver.

The disclosure also relates to a method of producing an earpiece for a hearing device of a user, where the method comprises: obtaining primary data representative of a position of at least part of the superior part of the ear canal of the user; obtaining secondary data representative of a position of the inferior concha cava of the user, manufacturing an ear canal part and a support structure for a primary sensor based on the primary data and the secondary data, wherein the ear canal part and the support structure is configured to transmit a force from the superior part of the ear canal of the user to the inferior concha cava. By providing an earpiece where the position of one, two or more anatomical parts of the ear are obtained, it is possible to construct an ear canal part and/or a support structure that provides the correct amount of force to the contact surfaces, inferior concha cava and superior part of the ear canal or any further contact surfaces, between the contact surfaces, so that the earpiece may be held in position using the force applied via contact surfaces via the ear canal part and/or the support structure. Thus, the positioning of the first contact surface of the ear canal part and the second part of the support structure may be provided to fit the ear of the user, so that the force is sufficient to hold the primary sensor in its position and to ensure that the comfort of the earpiece is optimal.

In one or more exemplary methods, the ear canal part and the support structure for the sensor may be provided as a customized part having an outer surface that corresponds with at least part of the shape of the ear canal and/or the concha cava of the user. The provision of a custom housing may ensure that the earpiece fits the user in an optimal manner, where the outer shape of the custom housing may have surfaces that match the surface areas of the outer ear of the user. The custom housing may be formed or moulded using a 3D model of the ear and the ear canal of the user. The support structure may be part of the housing and may be formed together with the housing. This means that the support structure may be formed and structured optimally to hold the ear canal part in its position, as well as maintaining the support structure positioned in such a way, that the force applied between the superior part of the ear canal and the inferior concha cava is optimal for the specific user. I.e. that the force between these two anatomical parts is applied in an optimum manner, thereby reducing risk that the user will tire when using the earpiece.

In one or more exemplary methods, the manufacturing the ear canal part and the support structure may comprise forming a first cavity in the ear canal part and/or forming a second cavity in the support structure, the method comprising inserting a receiver in the first cavity and/or inserting the primary sensor in the second cavity. By providing a first cavity for the receiver and/or a second cavity for the primary sensor, the receiver and/or the primary sensors may be removably connected to the earpiece, and e.g. interchanged when necessary. Thus, if a primary sensor or a receiver is damaged or malfunctions it is relatively easy to remove the receiver and/or the sensor from their cavities and position a replacement sensor in the same cavity. The cavities may be open cavities, where the cavities provide through going opening from one side of the cavity to the other side of the cavity.

FIG. 1a shows an earpiece 1 having an ear canal part 2 and a support structure 3, where the support structure comprises a first part 4 and a second part 5. The ear canal part 2 comprises a first contact surface 6, where the ear canal part 2 is adapted to be inserted into the ear canal of a user, and where the first contact surface 6 is adapted to be positioned so that the first contact surface is in contact with the superior ear canal of the user. The ear canal part 2 is attached to the support structure 3, where in this exemplary embodiment, the support structure 3 and the ear canal part 2 are integral, i.e. that they are made out of a single material that is constructed without any joints. The ear canal part 2 optionally comprises a cavity 7, also denoted first cavity, for a receiver 8, where the receiver 8 extends into the cavity 7 where the first end 9 of the ear canal part 2 comprises a receiver opening (not shown). In this exemplary embodiment, the ear canal part 2 comprises a second 10, third 11, and fourth contact surfaces 12, where the contact surfaces 10, 11, 12 are adapted to contact the entire circumference of the ear canal of the user.

The support structure 3 comprises a first part 4 which is connected to a second end 13 of the ear canal part 2, and where the support structure extends outwards, and backwards, so that a bottom part 18 of the support structure follows the contours of the outer ear of the user, until it terminates at its second part 5. The second part 5 comprises a cavity 15, also denoted second cavity, for a sensor 16, where the sensor 16 is positioned inside the cavity, so that the bottom part of the primary sensor (shown in FIG. 3) is exposed through a lower opening (17 in FIG. 2a) on the bottom part 18 of the support structure, allowing the bottom part of the primary sensor to come into contact with the inferior concha cava of the user. The primary sensor 16 may be a PPG sensor, where the primary sensor is adapted to shine an infrared light into the skin surface of the user, and the reflection of the light can be used to extract measurement data from the skin, where the measurement data may e.g. be blood flow below the skin. Thus, the bottom part 18 of the support structure 3, may follow the contour of the ear, from the opening of the ear canal and towards the inferior concha cava, where the first part 4 of the support structure 3 attaches to the ear canal part 2 and follows along the bottom part 18 of the support structure 3, towards its second part 5, which holds the primary sensor.

The ear canal part 2 comprises a first contact surface 6, which is mechanically connected to the support structure 3 and the primary sensor 16, which may be positioned in the inferior concha cava, so that a force that is applied to the second part 5 of the support structure 3 and/or the sensor 16 may be opposed by a counterforce applied to the first contact surface 46. Thus, when the earpiece 1 is positioned inside the ear of a user, the force applied to the first contact surface 6 and the second part 5 are in opposite directions, allowing the earpiece to be wedged in by the opposing forces, and thereby securing the earpiece 1 inside the ear of the user. The sensor 16 may have a skin contacting surface and/or the support structure 3 may have a skin contacting surface to provide the counterforce to the first contact surface 6.

Figure 1B:
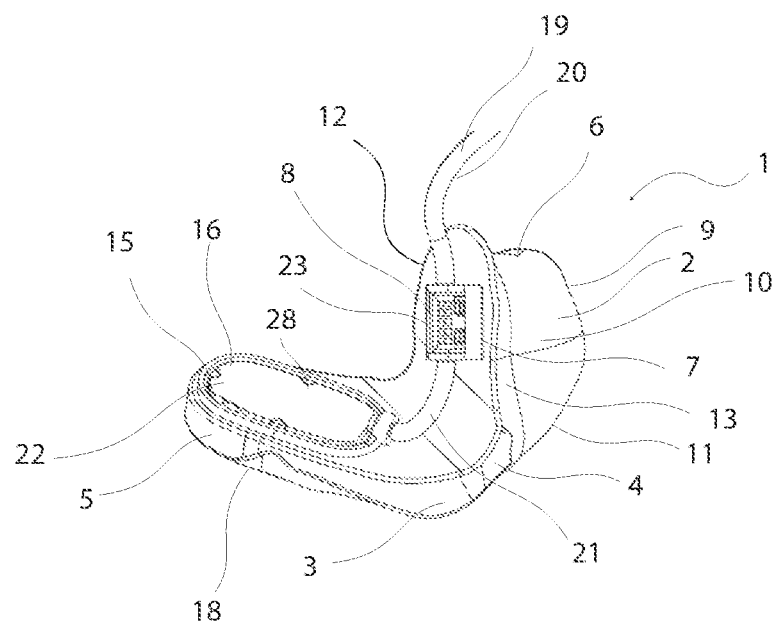

The earpiece shown in FIG. 1a, comprises an electrical wire 19, which can be utilized to connect the earpiece 1 to e.g. a BTE housing (not shown) where the first part 20 of the electrical wire 19 extends from the BTE housing to the receiver 8. FIG. 1b shows where at least some of the electrical connections 23 of the wire 19 are connected to the receiver 8, and where at least some of the electrical connections of the wire extend onwards via the second part 21 of the wire 19 and into the sensor housing 22. The electrical connections 23 that extend into the receiver are e.g. adapted to send electrical sound signals to the receiver, while the electrical connections 23 that extend along the second part of the wire 21 can be utilized to power the sensor, and to send and receive sensor data, and transmit via the electrical wire 19 into the BTE housing.

Figure 2A:
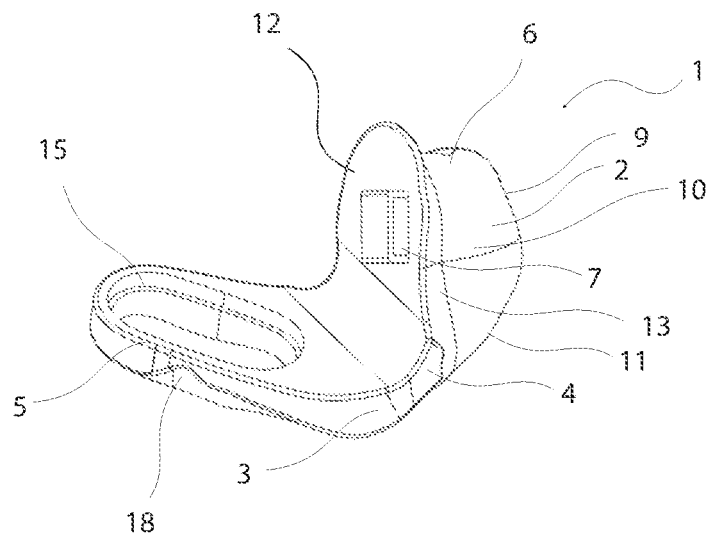
FIG. 2a shows an exemplary earpiece and FIG. 2b shows an exemplary receiver and primary sensor.
Figure 2B:
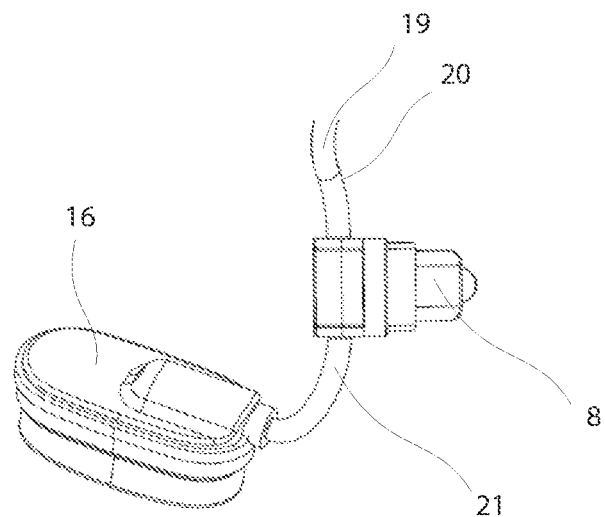

FIG. 2a shows the moulded earpiece of FIG. 1 without a primary sensor and the receiver, where the opening 17 in the bottom part 18 of the support structure is shown. In this view, the receiver cavity 7 and the sensor cavity 15 are shown, where the sensor 16 and/or receiver 8 shown in FIG. 2a may be removably attached to the earpiece 1.

Figure 3:
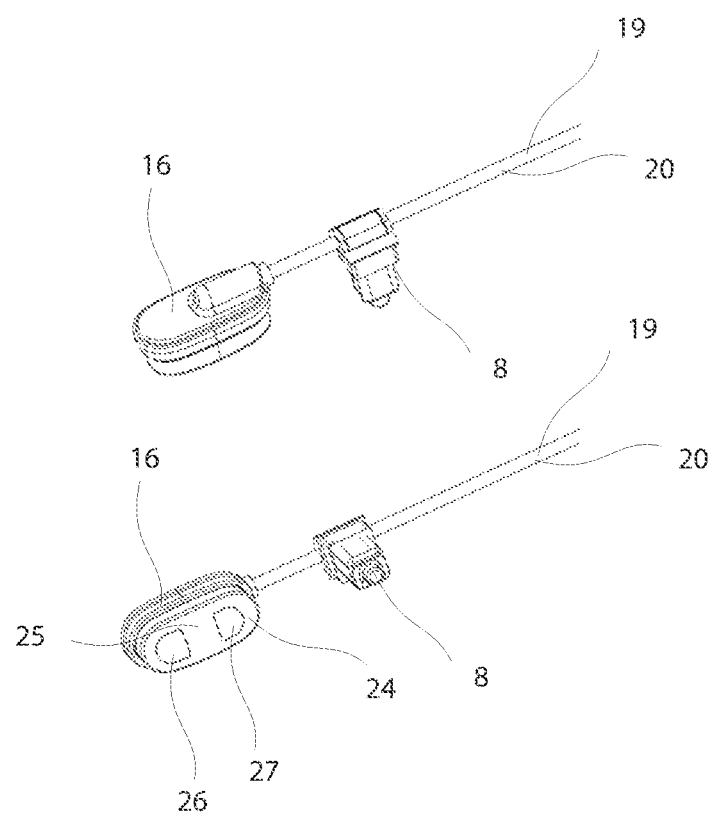
FIG. 3 shows an exemplary sensor and receiver in a perspective side view and perspective bottom view.

FIG. 3 shows the sensor 16, the receiver 8, and the electrical wire 19. In this view, the bottom part 24 of the sensor is shown, where the bottom part 24 comprises a skin contacting surface 25, a first window 26 and a second window 27, where the transmission and sensing of the light of the PPG sensor may be measured using traditional parts for a PPG sensor, where the windows are translucent, allowing light to pass from the inside of the sensor housing 28 through the windows 26, 27, and into the skin of the user, and where the light which is reflected from the skin and subcutaneous areas of the body, can be received by the sensor. The received signals are then transmitted via the electrical connections 23 towards e.g. a BTE housing, which can store, process or otherwise utilize the signals for representing physiological data of the user.

Figure 4A:
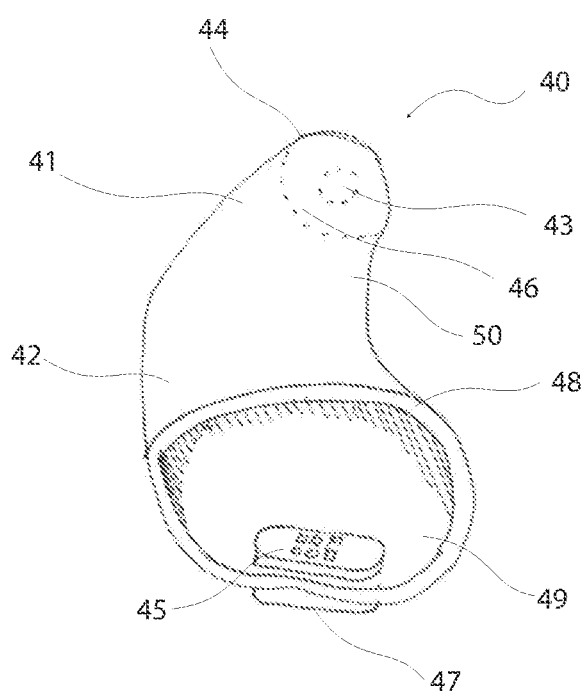
FIGS. 4a and 4b show an exemplary custom earpiece and an exemplary custom earpiece having a minimal mold.

FIG. 4a shows another example of an earpiece in accordance with the disclosure, in a schematic form, having custom mould earpiece 40, having an ear canal part 41, support structure 42, a receiver opening 43 in the first end 44 of the ear canal part 41, a primary sensor 45. The support structure 42 also comprises an upper part 48, so that the support structure is substantially annular in the second part 49 of the support structure 42. The ear canal part 41 comprises a first contact surface 46, which is mechanically connected to the support structure 42 and the sensor 45, which may be positioned in the inferior concha cava, so that a force that is applied to the skin contact surface 47 of the sensor 45 may be opposed by a counterforce applied to the first contact surface 46. Thus, when the earpiece 40 is positioned inside the ear of a user the force applied to the first contact surface 46 and the skin contact surface 47 are in opposite directions, allowing the earpiece to be wedged in by the opposing forces, and thereby securing the earpiece inside the ear of the user.

Figure 4B:
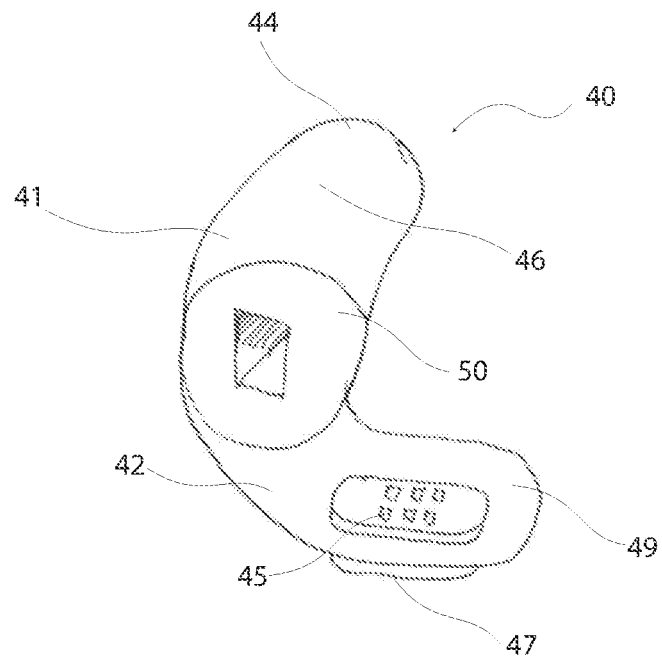

FIG. 4b shows a similar housing to that shown in FIG. 4a, where the upper part 48 of the support structure 42 has been removed, and the sensor 45 and the second part 49 extend from a second end 50 of the ear canal part 41, into the inferior concha part of the ear of the user. The support structure 42 is relatively rigid, so that a force that is applied to the second part 49 of the support structure 42 is transferred directly towards the first contact surface 46, allowing the opposing force to hold the earpiece 40 in its position in the ear of the user.

Figure 5A:
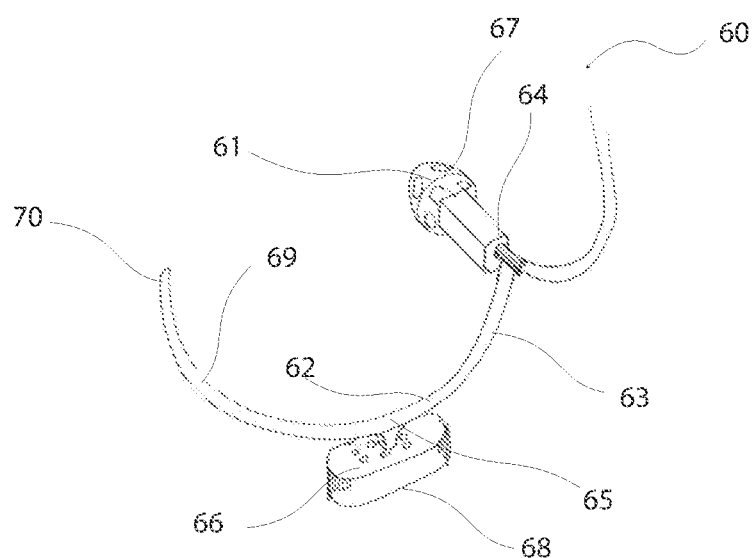
FIG. 5a-5c show three versions of earpieces having a support structure having a third part.

FIG. 5a shows an earpiece 60, where the earpiece comprises an ear canal part 61, a support structure 62, having a first part 63 which is connected to a second end 64 of the ear canal part 61, and a second part 65 of the support structure 62, which is connected to a sensor 66. The ear canal part comprises a first contact surface 67, which is adapted to contact the superior part of the ear canal, and where a force may be transmitted from a skin contacting surface 68 of the sensor 66 and to the first contact surface 67, allowing a force applied between the two surfaces to wedge the earpiece 60 in its position. In this example, the support structure comprises a third part 69, which is in a opposite direction from the first part, where the third part 69 may be utilized to apply a further support to the earpiece 60, by providing a second skin contacting surface 70, which may be utilized to contact a part of the ear which is not the ear canal or the inferior concha cava. The skin contacting surface may e.g. be used to contact the helix, Superior crus of antihelix, the cymba, or other parts of the outer ear of the user, to provide a further counterforce to either the first contact surface or the skin contacting surface of the sensor.

Figure 5B:
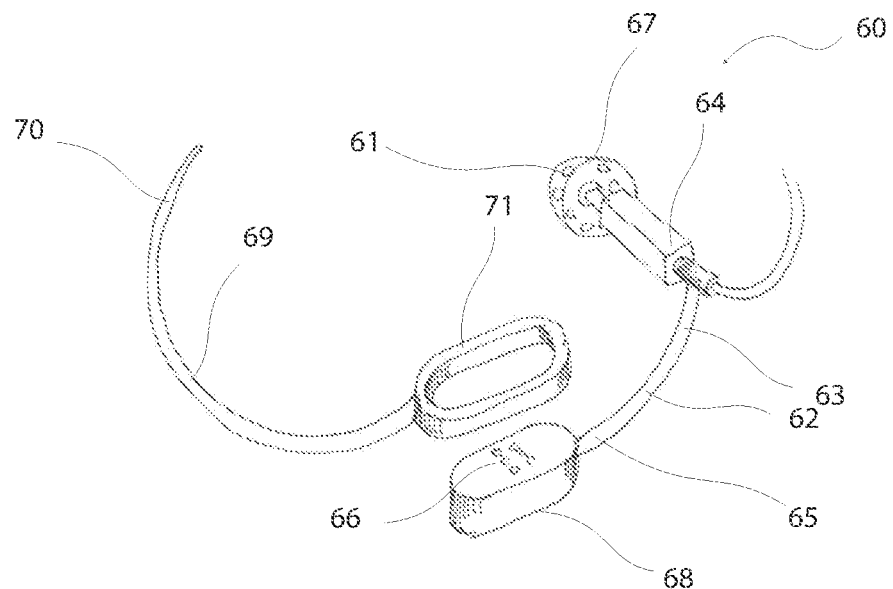

FIG. 5b shows a similar earpiece 60 to that shown in FIG. 5a, where the third part 69 is detachable from the second part 65. The third part 69 may be provided with a coupling member 71, which may be coupled to the second part 65 and/or the sensor 66. The coupling part may be provided in such a manner that any force that is applied to the third part 69 is transferred to the second part 65. Thus, when the coupling member 71 is attached to the second part 65 or the sensor 66, skin contacting surface of the third part may be used to provide further force, in a different direction, to the sensor and/or the ear canal part.

Figure 5C:
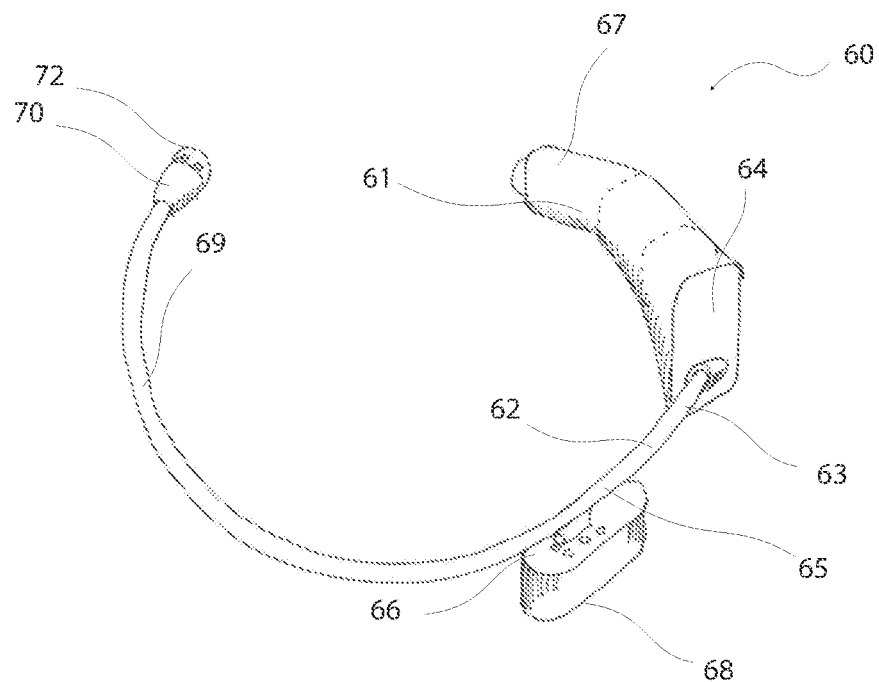

FIG. 5c is a yet further embodiment of an earpiece, of an ITE device, where the ear canal part 61 comprises a power source, a processor, and the third part 69 of the support structure, comprises a microphone 72. The microphone may be adapted to provide the second skin contacting surface 70, and the electrical connection between the ear canal part and the sensor, as well as the electrical connection to the microphone may be embedded in the support structure 62.

Figures 6A, 6B:
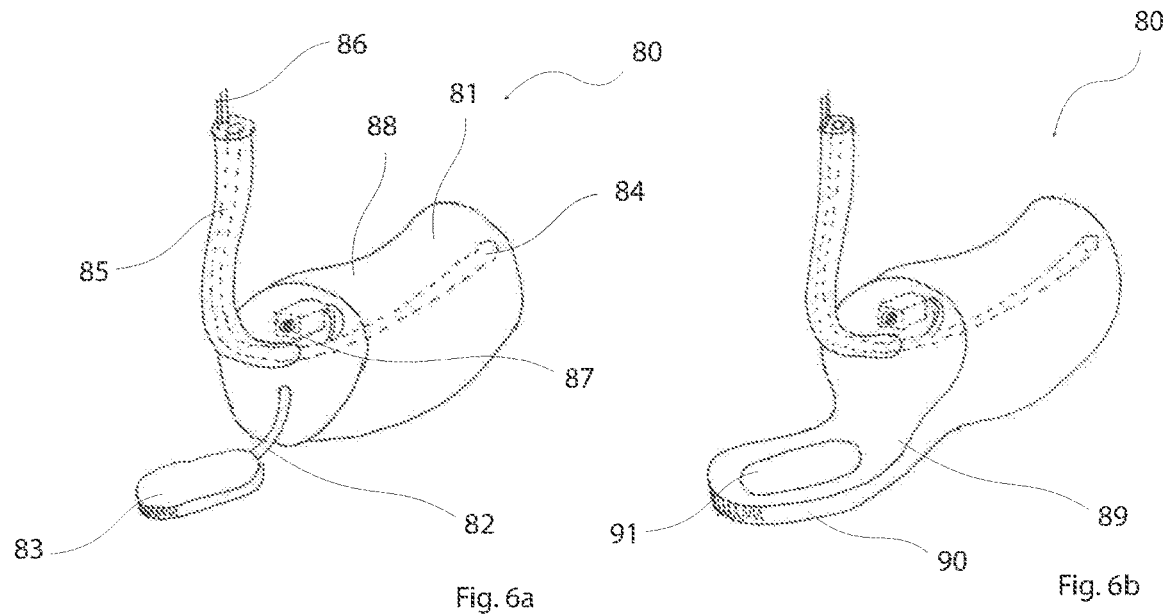
FIGS. 6a and 6b show exemplary earpieces for a BTE hearing device.

FIG. 6a shows one exemplary earpiece 80, comprising an ear canal part 81, support structure 82, sensor 83, having a receiver opening 84, where the receiver is in the BTE device, and the opening 84 is a sound path. The ear canal part 81 is connected to a BTE housing via a sound tube 85, where the sound tube encompasses electrical connections 86, that are adapted to connect the sensor 83 to the BTE housing, and to connect a microphone 87 to the BTE housing. The support structure 82 in this example may comprise a sensor wire 82, which may have a rigidness to force the sensor towards the skin surface of the user, when the first contact surface 88 of the ear canal part 61 is in contact with the superior ear canal, providing the opposing force.

FIG. 6b shows the same as in FIG. 6a, where the difference is that the support structure has been provided in the form of a support structure having a first part 89 connected to the ear canal part 81, and a second part 90 accommodating the sensor, e.g. in a sensor cavity 91.

Figures 7A, 7B:
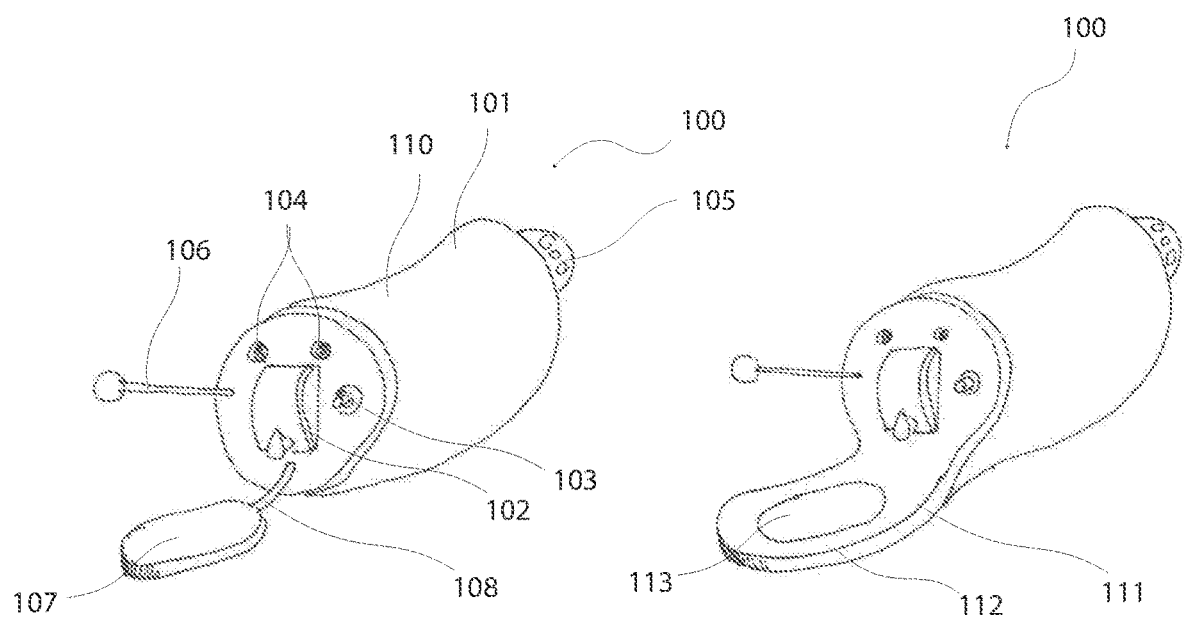
FIGS. 7a and 7b show exemplary earpieces for an ITE hearing device.

FIG. 7a shows one exemplary earpiece 100, which may be an ITE hearing device, where the earpiece 100 comprises an ear canal part 101, battery door 102, control button 103, one or two microphones 104, wax filter 105, pull out wire 106, sensor 107, support structure 108. The support structure 108 in this example may comprise a sensor wire 109, which may have a rigidness to force the sensor towards the skin surface of the user, when the first contact surface 110 of the ear canal part 101 is in contact with the superior ear canal, providing the opposing force.

FIG. 7b shows the same as in FIG. 7a, where the difference is that the support structure has been provided in the form of a support structure having a first part 111 connected to the ear canal part 101, and a second part 112 accommodating the sensor, e.g. in a sensor cavity 113.

The use of the terms "first", "second", "third" and "fourth", "primary", "secondary", "tertiary" etc. does not imply any particular order, but are included to identify individual elements. Moreover, the use of the terms "first", "second", "third" and "fourth", "primary", "secondary", "tertiary" etc. does not denote any order or importance, but rather the terms "first", "second", "third" and "fourth", "primary", "secondary", "tertiary" etc. are used to distinguish one element from another. Note that the words "first", "second", "third" and "fourth", "primary", "secondary", "tertiary" etc. are used here and elsewhere for labelling purposes only and are not intended to denote any specific spatial or temporal ordering.

Furthermore, the labelling of a first element does not imply the presence of a second element and vice versa.

Although features have been shown and described, it will be understood that they are not intended to limit the claimed invention, and it will be made obvious to those skilled in the art that various changes and modifications may be made without departing from the spirit and scope of the claimed invention. The specification and drawings are, accordingly to be regarded in an illustrative rather than restrictive sense. The claimed invention is intended to cover all alternatives, modifications, and equivalents.

LIST OF REFERENCES

1 Earpiece
2 Ear canal part
3 Support structure
4 First part of support structure
5 Second part of support structure
6 First contact surface
7 Receiver cavity
8 Receiver
9 First end of ear canal part 10 Second contact surface
11 Third contact surface
12 Fourth contact surface
13 Second end of ear canal part
15 Sensor cavity
16 Sensor (Primary)
17 Lower opening in support structure
18 Bottom part
19 Electrical wire
20 First part of electrical wire
21 Second part of electrical wire
22 Sensor housing
23 Electrical connections
24 Bottom part of sensor
25 Skin contacting surface
26 First window
27 Second window
28 Inside of sensor housing
40 Earpiece
41 Ear Canal part
42 Support structure
43 Receiver opening
44 First end of ear canal part
45 Primary sensor
46 First contact surface
47 Skin contacting surface
48 Upper part of support structure
49 Second part of support structure
50 Second end of ear canal part
60 Earpiece
61 Ear Canal part
62 Support structure
63 First part of support structure
64 Second end of ear canal part
65 Second part of support structure
66 Sensor
67 First contact surface
68 Skin contacting surface of sensor
69 Third part of support structure
70 Second skin contacting surface
71 Coupling member
72 Microphone
80 Earpiece
81 Ear Canal part
82 Support structure
83 Sensor
84 Receiver opening
85 Sound tube
86 Electrical connections
87 Microphone
88 First contact surface
89 First part of support structure
90 Second part of support structure
91 Sensor cavity
100 Earpiece
101 Ear canal part
102 Battery door
103 Control button
104 Microphones
105 Wax filter
106 Pull out wire
107 Sensor
108 Support structure
109 Sensor wire
110 First contact surface
111 First part of support structure
112 Second part of support structure
113 Sensor cavity.

The invention claimed is:

1. An earpiece for a hearing device, comprising:
an ear canal part to be introduced into an ear canal of a user, the ear canal part comprising a first contact surface configured to contact a superior part of the ear canal of the user;
a primary sensor, where the primary sensor is configured to measure signals from a skin surface of the user; and
a support structure comprising a first part and a second part, wherein the first part of the support structure is attached to the ear canal part, wherein the second part of the support structure is attached to the primary sensor, and wherein the second part of the support structure is configured to position the primary sensor at a location that is outside the ear canal of the user, the location having an elevation that is below an elevation of an ear canal opening of the user;
wherein the support structure is configured to apply a force to press the primary sensor towards the skin surface of the user.

2. The earpiece according to claim 1, wherein the ear canal part comprises a housing having an outer surface, where the outer surface of the housing has a shape corresponding with an ear canal surface of the ear canal.

3. The earpiece according to claim 1, wherein the ear canal part comprises a first end having a receiver opening and/or a second end which is attached to the support structure.

4. The earpiece according to claim 1, wherein the support structure comprises a third part which is connected to the first part and/or the second part, and wherein the third part of the support structure is configured to contact and transmit a force from a surface area of an outer ear of the user to the skin surface from which the primary sensor measures the signals.

5. The earpiece according to claim 1, wherein the primary sensor is a Photoplethysmogram sensor.

6. The earpiece according to claim 1, wherein the first part and/or the second part of the support structure has a shape that corresponds with at least a part of a concha cava of an ear of the user.

7. The earpiece according to claim 1, wherein the ear canal part comprises a housing, and wherein the housing is a custom housing corresponding to a 3D shape of an outer ear and/or the ear canal of the user.

8. The earpiece according to claim 1, wherein the first contact surface is a non-elastic first contact surface.

9. The earpiece according to claim 1, wherein the second part of the support structure is non-elastic.

10. The earpiece according to claim 1, wherein the ear canal part comprises a cavity for accommodating a receiver.

11. The earpiece according to claim 10, further comprising the receiver, wherein the receiver is removably attached to the ear canal part.

12. The earpiece according to claim 1, wherein the support structure comprises a cavity for accommodating the primary sensor.

13. The earpiece according to claim 12, wherein the primary sensor is removably attached to the support structure.

14. The earpiece according to claim 1, wherein at least a part of the force is supported by the superior part of the ear canal.

15. The earpiece according to claim 1, wherein the support structure is integrally formed with the ear canal part.

16. The earpiece according to claim 1, wherein the support structure is attached to, or is a part of, a faceplate of the ear canal part.

17. The earpiece according to claim 1, wherein the support structure comprises an elongated member.

18. A hearing device comprising the earpiece of FIG. 1, a BTE unit, and an electrical wire connecting a receiver in the ear canal part and/or the primary sensor to the BTE unit of the hearing device.

19. The earpiece according to claim 1, wherein the second part of the support structure is configured to position the primary sensor at a concha cava of the user.

20. The earpiece according to claim 19, wherein the second part of the support structure is configured to position the primary sensor at a lower part of the concha cava of the user.

21. The earpiece according to claim 1, wherein the second part of the support structure has a downward facing configuration.

* * * * *